(12) United States Patent
Gaylo et al.

(10) Patent No.: US 6,341,952 B2
(45) Date of Patent: Jan. 29, 2002

(54) FABRICATION OF TISSUE PRODUCTS WITH ADDITIVES BY CASTING OR MOLDING USING A MOLD FORMED BY SOLID FREE-FORM METHODS

(75) Inventors: Christopher M. Gaylo, Princeton Junction, NJ (US); Walter Flamenbaum; Miles J. Flamenbaum, both of New York, NY (US)

(73) Assignee: Therics, Inc., Princeton, NJ (US)

( * ) Notice: Subject to any disclaimer, the term of this patent is extended or adjusted under 35 U.S.C. 154(b) by 0 days.

(21) Appl. No.: 09/768,778

(22) Filed: Jan. 22, 2001

Related U.S. Application Data

(63) Continuation of application No. 09/045,661, filed on Mar. 20, 1998, now Pat. No. 6,261,493.
(60) Provisional application No. 60/039,374, filed on Mar. 20, 1997.

(51) Int. Cl.[7] .................................................. B28B 1/26
(52) U.S. Cl. ......................... 425/84; 425/85; 425/546; 425/134; 623/15.11; 623/15.12; 623/901
(58) Field of Search ..................... 425/84, 85, 546; 425/134; 623/15.11, 15.12, 901

(56) References Cited

U.S. PATENT DOCUMENTS

| | | | |
|---|---|---|---|
| 4,131,648 A | 12/1978 | Choi et al. | 424/22 |
| 5,204,055 A | 4/1993 | Sachs et al. | 419/2 |
| 5,340,656 A | 8/1994 | Sachs et al. | 428/546 |
| 5,387,380 A | 2/1995 | Cima et al. | 264/69 |
| 5,490,882 A | 2/1996 | Sachs et al. | 134/1 |
| 5,490,962 A | 2/1996 | Cima et al. | 264/22 |
| 5,518,680 A | 5/1996 | Cima et al. | 264/401 |
| 5,681,572 A | 10/1997 | Seare, Jr. | 424/400 |
| 5,711,172 A | 1/1998 | Boyce | 249/112 |
| 5,869,170 A | 2/1999 | Cima et al. | 428/304.4 |
| 6,176,874 B1 * | 1/2001 | Vacanti et al. | 623/1.44 |
| 6,283,997 B1 * | 9/2001 | Garg et al. | 623/16.11 |

OTHER PUBLICATIONS

Lee et al., "Protein–Resistant Surfaces Prepared by PEO–Containing Block Copolymer Surfactants," *Journal of Biomedical Materials Research*, 23:351–368, 1989.

Sachs et al., "CAD–Casting: Direct Fabrication of Ceramic Shells and Cores by Three Dimensional Printing," *Manufacturing Review, American Society of Mechanical Ebgineers*, 5(2):117–126, Jun., 1992.

* cited by examiner

*Primary Examiner*—Nam Nguyen
*Assistant Examiner*—Joseph S Del Sole
(74) *Attorney, Agent, or Firm*—Seed Intellectual Property Law Group PLLC

(57) ABSTRACT

A system for molding a tissue or substitute tissue product in a mold having an exterior surface, and an interior surface, wherein at least one portion of the interior surface is porous and whose pores are in continuous communication with the exterior surface, and wherein said mold can be fabricated using solid free-form fabrication techniques is disclosed.

15 Claims, 1 Drawing Sheet

FABRICATION OF TISSUE PRODUCTS WITH ADDITIVES BY CASTING OR MOLDING USING A MOLD FORMED BY SOLID FREE-FORM METHODS

CROSS-REFERENCE TO RELATED APPLICATION

This application is a continuation of pending U.S. patent application No. 09/045,661, filed Mar. 20, 1998, now U.S. Pat. No. 6,261,493 which is based on U.S. Provisional Patent Application No. 60/039,374, filed Mar. 20, 1997.

FIELD OF THE INVENTION

The present invention is in the area of methods for fabricating molds to be used in manufacturing molded medical products, wherein the molds are fabricated using computer-aided design (CAD) in combination with solid free-form fabrication (SFF) technology. More particularly, the present invention is in the area of methods for fabricating molds for making molded tissue products.

BACKGROUND OF THE INVENTION

Solid free-form fabrication (SFF) techniques are known which can be used to manufacture complex objects from a variety of materials. These objects can be used as articles of manufacture themselves, or they can be used as molds to create molded articles. The SFF methods can be adapted for use with a variety of polymeric, inorganic and composite materials to create mold structures with defined compositions, strengths, and densities, using computer aided design (CAD).

SFF techniques include stereo-lithography (SLA), selective laser sintering (SLS), ballistic particle manufacturing (BPM), fusion deposition modeling (FDM), and three dimensional printing (3DP). The present invention can be practiced with any of these SFF techniques. A preferred way of practicing the invention is with the use of three dimensional printing for fabricating the molds of the invention. 3DP is used to create molds which can be used for molding products which comprise tissue from human or other animal sources. SFF techniques can be used to form molds which have at lease one porous portion on the interior surface of the molds, where these porous portions are in communication with the exterior of the molds. According to the teachings of the invention, tissue materials can be molded into a broad variety of shapes by introducing a mixture containing tissue material into the interior of a mold according to the teachings of the invention with the tissue material mixed with one or more fluid tissue matrix components. The fluid tissue matrix component or components can be withdrawn from the tissue material through the porous portion of the mold, to the exterior of the mold. A molded tissue product is thereby produced which can be then released from the mold. Optionally, one or more additives may be included in the pore space of the mold of the invention before carrying out molding of a tissue product, and the additive if used can be removed during the molding process by withdrawing the additive through the porous structure of the mold to the mold exterior.

The macrostructure and porosity of the mold can be manipulated by controlling printing parameters, the type of polymer and particle size, as well as the solvent and/or binder. Porosity of the matrix walls, as well as the matrix per se, can be manipulated using SFF methods, especially 3DP.

SUMMARY OF THE INVENTION

SFF methods can be used to fabricate a mold which can then be used for the subsequent fabrication of a tissue product to be used in patients. The tissue product to be made can be composed primarily of tissue, can be composed primarily of substitute tissue products, or can be composed of a blend or mixture of natural and synthetic materials intended to replace tissue in a patient. The fabrication of this tissue product using such a mold may be done using either gravity or pressure casting or molding techniques. According to the teachings of the present invention, at least one portion of the interior surface of the SFF prepared mold is porous and in porous communication with the exterior of the mold of the invention. The mold of the invention allows casting or molding of a tissue product to be more easily carried out because a more fluid mixture of tissue containing material can be introduced into a mold of the invention. Excess fluid or other excess components of the mixture containing the tissue material can be drawn from the mold selectively through the porous interior surface portion of the mold, concentrating the tissue product within the interior of the mold. Means for removing the excess fluid or other components can include a simple pump, such as a piston or rotary pump. A rough analogy to the method of the invention may be made to slip casting in the ceramics industry, where a ceramic material with excess water (slip) is introduced into a mold for pourability and then the excess water is extracted through the walls of the ceramic mold. By applying SFF processes to the fabrication of a mold, the mold itself can incorporate features which allow selected components of a tissue mixture to be molded to be absorbed or extracted through the walls of the mold. This permits a tissue mixture to comprise a component to facilitate pouring or injecting of the tissue mixture into the mold, with the ability to reduce or extract a selected component from the tissue mixture once the mixture is in the mold, enabling improved or augmented implantation or operating characteristics of the final molded tissue product.

Using the teaching of the present invention, a SFF fabricated mold is used to fully or selectively control the materials composition of the mold itself as well as the micro- and macro-architecture of the mold. For example, the mold may be fabricated from a ceramic material which is made with a microstructure that will selectively allow the absorption or extraction of fluid from a tissue mixture, such fluid having been mixed with the tissue to facilitate pouring or injection of the mixture into the mold. The porosity of the mold can be varied depending on the tissue mixture component to be extracted, or channels or pores may be introduced in certain areas of the mold as the mold is being fabricated, to allow extraction of tissue mixture components only from selected regions of the tissue being molded. A main advantage of the present invention is that it allows a tissue containing mixture to be formulated for flowability into a mold, along with the ability to absorb or extract selected components from said mixture during the molding process, optimizing the actual final tissue product's characteristics. This is a significant advance from conventional approaches for molding tissue products, which are currently molded using non-porous molds. The conventional method for molding tissue products requires that the tissue/additive composition ratio remain the same throughout the molding or casting process and in the final molded or cast product. This results in a compromise being made between the ease of molding and the desired properties of the final tissue product. And, since SFF techniques such as three dimensional printing are used to fabricate a mold, product geometries that are unavailable using conventional mold approaches or machining methods can be readily achieved. Such geometries include undercuts, overhangs and recurved surfaces.

BRIEF DESCRIPTION OF THE DRAWINGS

A full understanding of fabrication of molds for use according to the present invention may be had by reading the following detailed description, and may be aided by consideration of the drawing, wherein.

DETAILED DESCRIPTION OF THE PREFERRED EMBODIMENT

Figure 1:
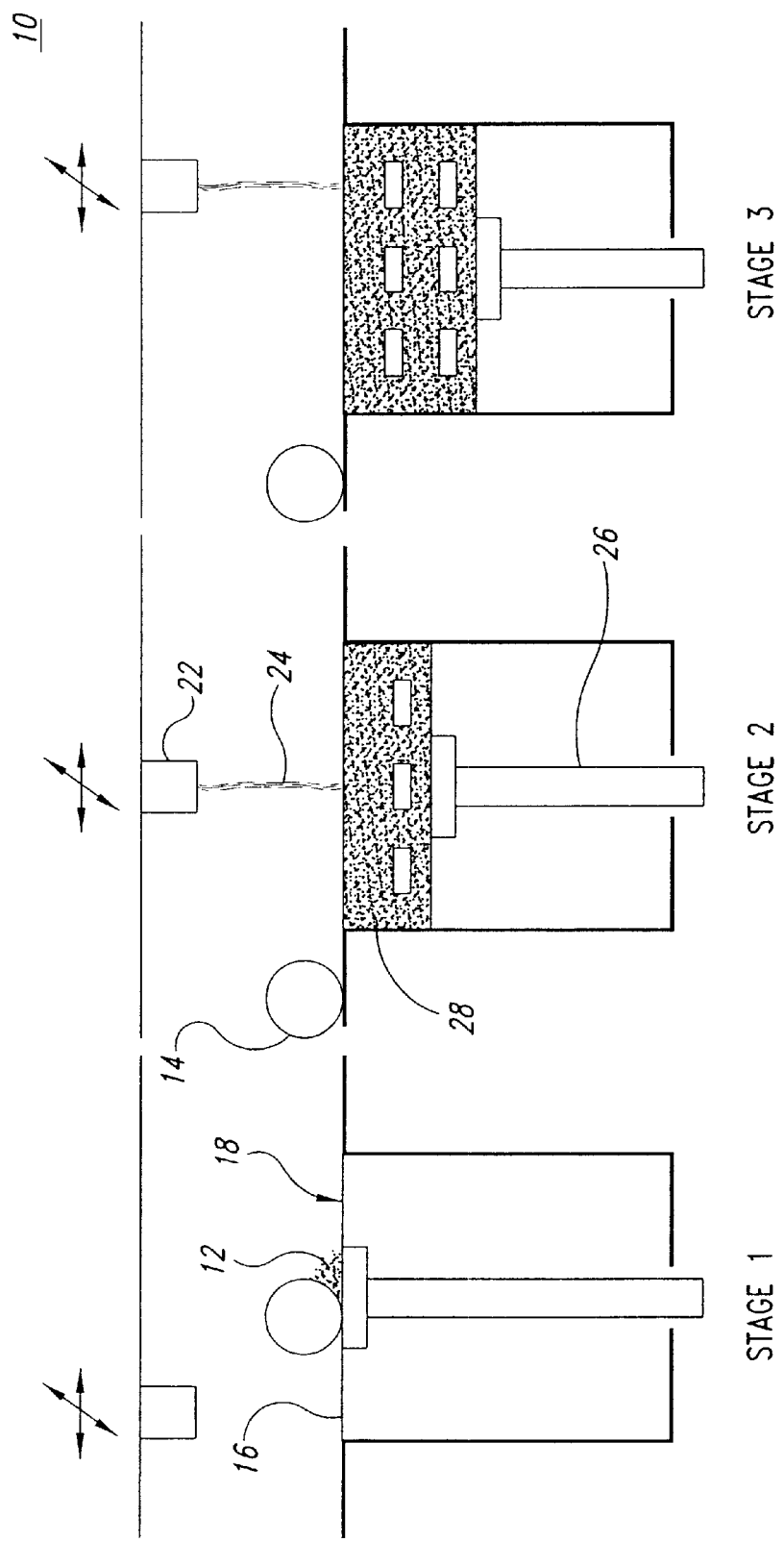
FIG. 1 is a schematic drawing of one embodiment of the three dimensional printing process of the invention.

Solid free-form fabrication methods offer several advantages for constructing molds for molding tissue products. Molded tissue products for implantation into patients can be constructed to fit the individual patient, individual cell type or organ structure. SFF methods can be used to selectively control the composition within the build plane as the mold is constructed by varying the composition of printed material. Unconventional microstructures, such as those with complicated porous networks or unusual composition gradients, can be designed at a CAD terminal and built through an SFF process such as 3DP. Complex resorbable or erodible tissue products can be built using the method of the invention.

Three dimensional printing (3DP) is described by Sachs, et al., "CAD-Casting: Direct Fabrication of Ceramic Shells and Cores by Three Dimensional Printing: Manufacturing Review 5 (2), 117–126 (1992) and U.S. Pat. No. 5,204,055, the teachings of which are incorporated herein by reference. Suitable devices for carrying out three dimensional printing include both those with a continuous jet stream print head and a drop-on-demand (DOD) print head. A continuous jet head provides for a fluid that is pressure driven through a small orifice. Droplets naturally break off at a frequency that is a function of the fluids properties and the orifice diameter. Either single jet or multiple jet print heads can be used in the method of the present invention. The use of multiple jet heads is preferred.

A DOD print head utilizes individual solenoid valves that run at frequencies up to 1.2 kHz. Fluid is also pressure driven through these valves and a small orifice is downstream of the valves to ensure accurate and repeatable droplet size.

Both raster and vector apparatuses can be used. When using DOD a raster apparatus provides that the print head goes back and forth across the bed with the jet turning on and off. A continuous jet is always on, and a vector apparatus is used similar to an x-y printer.

3DP is used to create a solid mold by ink-jet printing a binder onto selected areas of sequentially deposited layers of powder or particulates. In the following description, the terms "powder" and "particulates" are used interchangeably. Each layer is created by spreading a thin layer of powder over the surface of a powder bed. In a preferred embodiment, a movable powder piston is located within a cylinder, with a powered roller to deliver dispensed powder to a receiving platform located adjacent to the powder feeder mechanism. Operation consists of raising the feed piston a predetermined amount for each increment of powder delivery. The roller then sweeps across the surface of the powder feeder cylinder and deposits it as a thin layer across the receiving platform immediately adjacent to the powder feeder. The powder feeding piston is then lowered as the roller is brought back to the home position, to prevent any back delivery of powder.

The powder piston and cylinder arrangement can also consist of multiple piston/cylinders located in a common housing, which would be used to dispense multiple powders in the following sequence:

1. Line up the first desired powder cylinder with the rolling/delivery mechanism,
2. Increment the movable position piston up to deliver an incremental amount of powder,
3. Activate roller to move powder to receiving platform,
4. Lower the powder piston driving mechanism,
5. Laterally slide the powder feeder housing such that the next desired powder cylinder is lined up with the delivery mechanism,
6. Repeat steps 2, 3, 4 and 5,
7. Continue for as many different powders and/or powder layers as required.

This method of powder feeding can be controlled manually or be fully automated. Cross contamination of different powders is minimized since each powder is contained in its own separate cylinder. One of the advantages to this method is that only one piston raising/lowering mechanism is required for operation, regardless of the number of powder cylinders. By raising the powder for delivery rather than dropping it from above, problems associated with gravity based delivery systems such as "ratholing", incomplete feed screw filling/emptying and "dusting" with the use of fine powders is eliminated or minimized since only enough energy is introduced to move the powder up an incremental amount. The powder feeder housing, with its multiple cylinders and pistons, can also be designed as a removable assembly, which would minimize changeover times from one powder system to another.

The powder bed is supported by a piston which descends upon powder spreading and printing of each layer (or, conversely, the ink jets and spreader are raised after printing of each layer and the bed remains stationary). Instructions for each layer are derived directly form a computer-aided design (CAD) representation of the component. The area to be printed is obtained by computing the area of intersection between the desired plane and the CAD representation of the object. The individual sliced segments or layers are jointed to form the three dimensional structure. The unbound powder supports temporarily unconnected portions of the component as the structure is built but is removed after completion of printing.

The 3DP process is shown schematically in FIG. 1, wherein a 3DP apparatus is indicated generally by the number 10. Powder 12 is rolled from a feeder source (not shown) in stage 1 with a powder spreader 14 onto a surface 16 of a build bed 18 which comprises powder 28. The thickness of the spread layer is varied as a function of the type of dosage from being produced. Generally the thickness of the layer can vary from about 100 $\mu$m to about 200 $\mu$m. The print head 22 then deposits the binder (fluid) 24 onto the powder layer and the build piston 26 is lowered one layer distance. Powder is again rolled onto the build bed 18 and the process is repeated until the mold is completed (stages 2 and 3 of FIG. 1). The droplet size of the fluid is from about 50 $\mu$m to about 500 $\mu$m in diameter. Servo motors (not shown) are used to drive the various actions of the apparatus 10.

While the layers become hardened or at least partially hardened as each of the layers is laid down, once the desired final part configuration is achieved and the layering process is complete, in some applications it may be desirable that the form and its contents be heated or cured at a suitably selected temperature to further promote binding of the powder particles. In either case, whether or not further curing is required, the loose unbonded powder particles are removed using a suitable technique, such as ultrasonic cleaning, to leave a finished device.

As an alternative to ultrasonic cleaning, water soluble particulates may be used. Fabrication of structures with designed pore structures is a challenging task even with additive manufacturing processes such as 3DP. Cylindrical structures with radial pores of hundreds of microns in diameter can be fabricated, however, the removal of loose powder from the narrow channels requires a cumbersome manual clean up process. On solution is to employ mixtures of water soluble particulates (sodium chloride) with polymers used to fabricate specimens. The small particles then leach out to reveal an interconnected porous structure. While this technique is useful in fabricating a network of pores, control of pore architecture is lost. An improvement on this technique is to selectively deposit the soluble phase to form internal soluble patterns prior to building any external features. Water soluble materials such as poly(ethylene glycol) can be deposited on a flat surface prior to spreading a new layer of powder. This enables the process to build walls of soluble material. Loose powder can be spread after completion of the patterning. The external or insoluble features of the specimen can then be built by printing with binder solution. Following the requisite iterations of the patterning and printing processes, produces a dosage form that has intricate internal features that can be dissolved easily when immersed in an appropriate solvent. This concept can be used to fabricate molds with controlled internal pore channels.

Construction of a 3DP component such as a mold can be viewed as the knitting together of structural elements that result from printing individual binder droplets into a powder bed. These elements are called microstructural primitives. The dimensions of the primitives determine the length scale over which the microstructure can be changed. Thus, the smallest region over which the concentration of bioactive agent can be varied has dimensions near that of individual droplet primitives. Droplet primitives have dimensions that are very similar to the width of line primitives formed by consecutive printing of droplets along a single line in the powder bed. The dimensions of the line primitive depend on the powder and the amount of binder printed per unit line length. A line primitive of about 500 $\mu$m width is produced if an ink jet depositing 1.1 cc/min of methylene chloride is made to travel at about 20 cm/sec over the surface of a polycaprolactone (PCL) powder bed with 45–75 $\mu$m particle size. Higher print head velocities and smaller particle size produce finer lines. The dimensions of the primitive seem to scale with that calculated on the assumption that the liquid binder or solvent needs to fill the pores of the region in the powder which forms the primitive.

A number of approaches have been described for fabricating tissue products or substitute tissue products for use in patients. It would be advantageous to construct molded tissue products or substitute tissue products with precisely controlled complicated shapes. This can be accomplished by using SFF techniques to make precisely controlled molds. SFF uses computer aided design technology which allows construction of individual molds for one time use which can have the complicated shape necessary to mold a tissue product of virtually any desired shape.

It is therefore an object of the present invention to provide a method for molding complex shaped tissue products, for use in patients.

It is another object of the present invention to provide methods and compositions for making complex tissue products of bioerodible or non-bioerodible materials or composites for either cell transplantation or matrix-guided tissue regeneration.

It is a further object of the present invention to provide methods that operate with high precision and reproducibility to produce molded tissue products.

It is a still further object of the present invention to produce molded tissue products which can selectively encourage the growth of one tissue type over another at specific sites by virtue of control of matrix components within the molded tissue products.

Several other SFF methods can be used in making molds for tissue products in accordance with the teachings of the invention. These include stereo-lithography, selective laser sintering, ballistic particle manufacturing, and fusion deposition modeling. These may briefly be described as follows.

Stereo-lithography (SLA) and Selective Laser Sintering (SLS)

SFF methods are particularly useful for their ability to control composition and microstructure on a small scale for the construction of these medical devices. The SFF methods, in addition to 3DP, that can be utilized to some degree as described herein are stereo-lithography (SLA), selective laser sintering (SLS), ballistic particle manufacturing (BPM), and fusion deposition modeling (FDM).

Stereolithography is based on the use of a focused ultra-violet (UV) laser which is vector scanned over the top of a bath of a photopolymerizable liquid polymer material. The UV laser causes the bath to polymerize where the laser-beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired device is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biocompatible polymeric materials.

SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation of Austin, Tx.

SLA and SLS are thus similar in that in both techniques, matter is laminated to make three dimensional shapes. Use of these methods to control composition is limited to one dimensional control since one can only vary the composition of each layer. Nonetheless, these methods can be useful for construction of drug delivery and tissue matrix devices where one dimensional compositional control is all that is desired or where only variation in porosity is desired. Controlled porosity can be built using SLA and SLS simply by specifying the laser path over the layer surface to include only those regions which are to remain in the device.

Ballistic Particle Manufacturing (BPM) and Fusion Deposition Modeling (FDM)

BPM uses an ink-jet printing apparatus wherein an ink-jet stream of liquid polymer or polymer composite material is used to create three-dimensional objects under computer control, similar to the way an ink-jet printer produces two-dimensional graphic printing. The device is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y.

FDM employs an x-y plotter with a z motion to position an extrudable filament formed of a polymeric material, rendered fluid by heat or the presence of a solvent. A suitable system is available from Stratasys, Incorporated of Minneapolis, Minn.

BPM, FDM and 3DP are related in the sense that all three approaches deposit matter in small areas. Thus, they offer the advantage that local composition can be specified and constructed for any desired three dimensional profile. The composition control is only limited by the resolution of the particular apparatus used for construction. FDM builds structures by extruding a fine filament of plastically deformable material through a small nozzle. The nozzle is directed over the built surface by appropriate x, y and z motion control so as to yield the desired three dimensional structure. Similarly, BPM involves motion control of an ink jet print head to deposit matter in the form of small droplets. Appropriate control of where the droplets are printed permits the construction of a desired three dimensional shape. 3DP uses two sources of material the material that makes up the porous layer and the material that is printed.

Local composition control using FDM and BPM requires the application of multiple printing or extrusion tools. A similar approach can be followed with 3DP by using multiple print-heads. Alternatively, multiple droplets may be printed into the same location when using 3DP to increase the local composition of the species contained in the printed solution.

Porosity control using BPM and FDM can be accomplished using procedures similar to those which can be practiced using 3DP, as described herein.

Formation of Composite Devices

Composite devices can be made by combining inorganic and organic components. In particular, it may be desired to increase the amount of polymer in the device above that which can be obtained by one-pass printing of a polymer solution into an inorganic powder bed, for example, by adding a polymer latex to the printing solution. Another method is to mix a polymer powder with an inorganic powder. Still another method is to spread only polymer powder in the bed, and print a dispersion of inorganic particles (up to 30 vol%) in a solvent which will bind the polymer powder together. An example of this is to print a solution of apatite particles in chloroform onto a PLA powder bed. Alternatively one can include a polymer binder with an inorganic dispersion, for example by adding 30% by volume particles to a 5% by weight solution of PLA in chloroform. In the extreme, the bed could contain no material at all; both the inorganic and organic material could be printed through the nozzle.

Bioactive agents which can be incorporated.

There are essentially no limitations on the bioactive agents that can be incorporated into the molds, although those materials which can be processed into particles using spray drying, atomization, grinding, or other standard methodology, or those materials which can be formed into emulsifications, microparticles, liposomes, or other small particles, and which remain stable chemically and retain biological activity in a polymeric matrix, are preferred. Bioactive agents also include compounds having principally a structural role, for example, hydroxyapatite crystals in a matrix for bone regeneration. The particles may have a size of greater than or less than the particle size of the polymer particles used to make the matrix.

Examples generally include proteins and peptides, nucleic acids, polysaccharides, nucleic acids, lipids, and non-protein organic and inorganic compounds, referred to herein as "bioactive agents" unless specifically stated otherwise. These materials have biological effects including, but not limited to, anti-inflammatories, antimicrobials, anti-cancer, antivitals, hormones, antioxidants, channel blockers, and vaccines. It is also possible to incorporate materials not exerting a biological effect such as air, radiopaque materials such as barium, or other imaging agents.

Controlling Porosity in Molds

Porosity in 3D printed devices can be created either at the level of the feature size (between 10 and 20 microns and greater) or at a sub-feature size level. At the level of the feature size, porosity is controlled by where the features are placed, and thus pore size and shape can vary in three dimensions.

Porosity at a subfeature size level can be created in a variety of ways.

(1) Printing a polymer solution onto a bed of particles which are not soluble in the polymer and which can be subsequently leached with a non-solvent for the polymer. In this case, the polymer which forms the device is printed onto a bed of particles such as salt, sugar, or polyethylene oxide. After the printing process is complete, the device is removed from the powder bed and placed in a nonsolvent for the polymer which will dissolve the particles. For example, polylactic acid in chloroform could be printed onto a bed of sugar particles, and the sugar can subsequently be leached with water.

(2) Printing a polymer solution onto a bed of particles which are partially soluble in the printed solvent. An example is printing a polylactic acid solution onto a bed of polyethylene oxide particles. This procedure may allow interpenetration of PEO into the surface of the PLA and improve surface properties of the final device. Following printing, the PEO can be leached with water.

(3) Printing a polymer solution onto a heated bed of polymer. An example is printing polylactic acid in chloroform onto a bed of PLA particles heated to 100.degree. C. The boiling point of chloroform is 60.degree. C., and it will thus boil on hitting the particle bed, causing a foam to form.

(4) Printing a polymer solution onto a bed containing a foaming agent.

(5) Printing with solvents which have only a small solubility for the powder. In this manner only a small amount of polymer is deposited at the necks between the particles leaving much of the original porosity in the powder bed. For example, PCL is only slightly soluble in acetone and acetone has a relatively high vapor pressure. Very little polymer is, therefore, dissolved before the solvent dries. Thus, the necks formed between the particles are small and the porosity of the resulting component is much like that of the original powder bed.

Molds Having Modified Surface Properties

Modifying surface properties in select regions of the mold is also important and can be accomplished by printing a solution containing surface-active agents into the regions or lines in between where the binder is printed. As used herein, a "surface-active agent" may be an agent which promotes cell adhesion, such as an RGD peptide, or a material which inhibits cell adhesion, such as a surfactant, for example, polyethylene glycol or a Pluronic. TM. (polypropylene oxid-polyethylene oxide block copolymers). The surface-active agent should in general be contained in a solvent immiscible with the solvent used to print the binder.

For example, it may be desirable to incorporate adhesion peptides such as the RGD adhesion peptide into certain channels (e.g., those for blood vessel ingrowth). An adhesion peptide, such as the peptide having a hydrophobic tail marketed by Telios (LaHoya, Calif.) as Peptite. TM., can be dissolved in water and printed into the "voids" using a second set of printing nozzles. Adding water, a relatively non-volatile solvent, can alter the kinetics of solvent removal from regions printed with binder. For example, adding water can slow solvent removal by occluding the surface area for evaporation, and can help decrease warpage. On contact with the polymer surface, the peptide will adsorb out of solution onto the polymer surface.

The surface can also be modified to prevent cellular adhesion. This may be accomplished, for example, by printing an aqueous solution of a pluronic. TM. (BASF) or poloxamer. TM. in the voids. The hydrophobic block of such copolymers will adsorb to the surface of the channels, with the hydrophilic block extending into the aqueous phase. Surfaces with adsorbed pluronics. TM. resist adsorption of proteins and other biological macromolecules. Other adhesion-preventing materials are described in Lee, J. H., J. Kopecek, et al., "Protein-resistant surfaces prepared by PEO-containing block copolymer surfactants." J. Biomed. Mat. Res, 23:351–368 (1989), the teachings of which are hereby incorporated by reference.

Printing the mold with surface active agents while the "walls" of the mold are still "wet" with organic solvent (such as chloroform) can enhance the adsorption of the adhesion-preventing material to the walls and can even allow the hydrophobic block to become blended into the surface, enhancing the stability of the resulting surface modification.

For the applications described above, 3DP offers at least three advantages over current technologies for fabricating tissue product molds: (1) tailored macroscopic shapes for making tissue products with complex shapes, (2) well-defined microstructure in the mold, which may include controlled pore size distribution and directionally oriented pores and channels, and (3) incorporation of materials into the mold during its fabrication.

As used herein, "tissue material" includes both soft tissues such as parenchymal tissue (liver, pancreas, intestine, etc.), blood vessels, skin, and connective tissues such as cartilage and bone. The "tissue material" as used herein may have its origin in any type of animal, including but not limited to mammalian and human animals.

The tissue material mixture or tissue substitute material to be molded can also contain one or more synthetic polymers, one or more biopolymers, and/or one or more inorganic materials. The use of these latter materials allows the method of the present invention to be flexible in creating tissue and tissue substitute products which are adaptable to a variety of needs in patients.

The synthetic polymers which can be selected for use may be selected from the list consisting of poly($\epsilon$-caprolactones), poly(hydroxy alkanoates), poly(glycolides), poly(lactides), poly(co-glycolide/lactide), polydioxanone, polyamino acids, poly($\gamma$-glutamic acid), poly(vinyl acetates), poly(vinyl alcohols), poly(ethylene-imines), poly(orthoesters), polyphosphoesters, polyphosphazenes, poly(tyrosine-carbonates), polyanhydrides, polyarylates, poly(ethylene glycols), poly(trimethylene carbonate), polyiminocarbonates, poly(oxyethylene-polyoxypropylene), poly($\alpha$-hydroxycarboxylic acid/polyoxyalkylene), polyacetals, and poly(propylene fumarates).

The biopolymers which can be selected for use may be selected from the group consisting of natural proteins (gelatin, collagen, fibrin, elastin, fibronectin, laminin), recombinant proteins (prolastin, pronectin, betasilk), glycosaminoglycans (hyaluronic acid, chondroitin sulfate, heparin), carbohydrates (cellulose, chitin, chitosan, dextrins, dextrans), carboxymethylcellulose, sodium hyaluronate, and proteoglycans.

The inorganic materials which can be used may be selected from the group consisting of calcium phophates, hydroxyapatites, bioactive glasses, demineralized bone particles, and calcium sulfates.

Optionally, the mold of the invention may be fabricated with the mold itself containing within its matrix certain additives. These additives include but are not limited to: pharmaceuticals (antibiotics or anti-inflammatories), hormones (somatotropin), growth factors (bone morphogenetic proteins), peptides (RGD fragments), amino acids, vitamins, enzymes (collagenase, peptidase, oxidase), cellular attractants (fibronectin, vitronectin), living cells (chondrocytes, bone marrow cells), natural tissue extract, fragments of natural tissue, and surface active agents (surfactants, PEG).

Components of tissue mixtures being molded which components can be absorbed or extracted through the walls of a mold in accordance with the invention include but are not limited to the following liquid substances or mixtures thereof: water, organic solvents (chloroform, ethanol, other aliphatic alcohols, acetone), polyhydroxy compounds (glycerol, polyethylene glycol, glycerol esters), sugars, fatty acid esters, and natural oils (soybean, castor, linseed, peanut).

Materials which can be used to fabricate a mold in accordance with the teachings of the invention include but are not limited to the following materials or mixtures thereof: plastics (polycarbonate, polysulfone, polymethylmethacrylate, polyetherimide), ceramics (alumina, colloidal silica, zirconia, zircon, silicon carbide), and metals (stainless steel, titanium).

Although mold construction varies with each tissue material type, the methods used for construction will typically be the same, optimized to create appropriate shapes and pore sizes. In general, interconnected pores or channels will extend from the exterior throughout the interior, typically between 0.15 and 0.5 mm in diameter, which are separated by walls approximately 30 to 100 microns thick, which are either solid or porous with an average pore size of approximately 5 to 40 microns.

Modifications and variations of the method and compositions described herein will be obvious to those skilled in the art from the foregoing detailed description. Such modifications and variations are intended to come within the scope of the appended claims.

What is claimed is:

1. A mold having an interior surface and an exterior surface, wherein said mold has at least one portion of said interior surface which is porous and whose pores are in continuous communication with said exterior surface, and wherein said mold comprises an additive useful for making a molded product for use as a tissue substitute, said additive selected from the group consisting of pharmaceuticals, hormones, growth factors, peptides, amino acids, vitamins, enzymes, cellular attractants, living cells, natural tissue extract, fragments of natural tissue, and surface active agents.

2. The mold of claim 1, wherein said mold is fabricated using a solid free-form fabrication technique.

3. The mold of claim 2, wherein said mold is fabricated using three dimensional printing.

4. The mold of claim 3, wherein said mold is adapted for coupling to a liquid removal means for removing a liquid substance from the interior surface of said mold to the exterior surface of said mold.

5. The mold of claim 4, wherein said liquid removal means is selected from a group consisting of a pump, a centrifuge, and gravity.

6. The mold of claim 5, wherein said liquid removal means is a pump.

7. The mold of claim 5, wherein said liquid removal means is a centrifuge.

8. The mold of claim 5, wherein said liquid removal means is gravity.

9. A system for manufacturing a molded product for use as a tissue substitute, comprising:
   a) a mold having an interior surface and an exterior surface, wherein said mold has at least one portion of said interior surface which is porous and whose pores are in continuous communication with said exterior surface, and wherein said mold comprises an additive, said additive selected from the group consisting of pharmaceuticals, hormones, growth factors, peptides, amino acids, vitamins, enzymes, cellular attractants, living cells, natural tissue extract, fragments of natural tissue, and surface active agents;
   b) introduction means for introducing into said mold a mixture comprising a solid component selected from the group consisting of bioerodible, non-bioerodible and composite materials, wherein said mixture further comprises a liquid substance at least a portion of which can pass through said pores; and
   c) liquid removal means for removing a portion of said liquid substance from said solid component by withdrawal through the at least one portion of said interior surface which is porous.

10. The system for manufacturing a molded product for use as a tissue substitute of claim 9, wherein said mold is fabricated using a solid free-form fabrication technique.

11. The system for manufacturing a molded product for use as a tissue substitute of claim 10, wherein said mold is fabricated using three dimensional printing.

12. The system for manufacturing a molded product for use as a tissue substitute of claim 9, wherein said liquid removal means is selected from a group consisting of a pump, a centrifuge, and gravity.

13. The system for manufacturing a molded product for use as a tissue substitute of claim 12, wherein said liquid removal means is a pump.

14. The system for manufacturing a molded product for use as a tissue substitute of claim 12, wherein said liquid removal means is a centrifuge.

15. The system for manufacturing a molded product for use as a tissue substitute of claim 12, wherein said liquid removal means is gravity

* * * * *